(12) United States Patent
Schilling et al.

(10) Patent No.: US 7,846,487 B2
(45) Date of Patent: *Dec. 7, 2010

(54) BIOLOGICALLY ACTIVE PRODUCTS

(75) Inventors: Marvin L. Schilling, Fort Smith, AR (US); Richard D. Fafard, Monson, MA (US)

(73) Assignee: Chick Cart Inc, Fort Smith, AR (US)

( * ) Notice: Subject to any disclaimer, the term of this patent is extended or adjusted under 35 U.S.C. 154(b) by 1291 days.

This patent is subject to a terminal disclaimer.

(21) Appl. No.: 11/343,013

(22) Filed: Jan. 30, 2006

(65) Prior Publication Data

US 2006/0127494 A1 Jun. 15, 2006

Related U.S. Application Data

(63) Continuation-in-part of application No. 09/964,120, filed on Sep. 25, 2001, now Pat. No. 7,083,820.

(60) Provisional application No. 60/273,005, filed on Mar. 5, 2001.

(51) Int. Cl.
*A23L 1/10* (2006.01)
*A61K 38/39* (2006.01)
*A61K 9/14* (2006.01)
*A61K 35/12* (2006.01)
*A61K 35/34* (2006.01)

(52) U.S. Cl. .................. 426/465; 426/665; 426/443; 426/455; 424/489; 424/520; 424/548; 514/2; 514/21

(58) Field of Classification Search .................. None
See application file for complete search history.

(56) References Cited

U.S. PATENT DOCUMENTS

| 4,250,139 | A |  | 2/1981 | Luck et al. |  |
| 4,404,033 | A |  | 9/1983 | Steffan et al. |  |
| 5,645,851 | A |  | 7/1997 | Moore |  |
| 6,162,787 | A | * | 12/2000 | Sorgente et al. | 514/2 |
| 7,083,820 | B2 | * | 8/2006 | Schilling et al. | 426/465 |

FOREIGN PATENT DOCUMENTS

JP 5902637 2/1987

* cited by examiner

*Primary Examiner*—Lakshmi S Channavajjala
(74) *Attorney, Agent, or Firm*—Bernd W. Sandt

(57) ABSTRACT

The present invention relates to dehydrated Type II collagen containing cartilage which has retained the collagen in its original crosslinked structure and which contains at least 40% by weight of the Type II collagen of an ionizable edible salt and which has a water content of less than 10%.

12 Claims, No Drawings

BIOLOGICALLY ACTIVE PRODUCTS

"This application is a continuation-in-part of U.S. application Ser. No. 09/964,120 filed Sep. 25, 2001, now U.S. Pat. No. 7,083,820, which claims the benefit of 60/273,005 filed on Mar. 5, 2001"

The present invention relates to biologically active products, which are safe for human consumption as well as for consumption by other life forms. More specifically the present invention relates to a dehydrated product that retains its original natural structure and thereby its biological activity and is sufficiently stabilized to allow commercial storage and sale of the product. This application is a continuation in part of copending application Ser. No. 09/964,120 filed Sep. 9, 2001.

BACKGROUND OF THE INVENTION

There are a large number of naturally occurring substances that have found medical and health applications in various fields but that must be processed to be suitable as a commercial product. Historically, maintaining the biological activity of certain potentially useful substances along with providing this to the intended recipient in a safe manner, particularly regarding pathogen safety and the control of deleterious enzyme activity, is costly and frequently results in a decrease of the efficacy as a result of denaturing of the biologically active material. Nevertheless there are several commercial fields that market products based on naturally occurring biologically active products, such as in the pharmaceutical and dietary supplement fields, food field, medical field, over-the-counter medicine field, and the cosmetic field.

One example of an application for such nutraceutical products is in the use of Type II collagen to alleviate the symptoms of arthritis sufferers. This compound is reported to work with the arthritis sufferer's immune system in a positive manner. As disclosed in the patents of Dr. Eugene Moore (U.S. Pat. Nos. 5,570,144, 5,529,786, 5,637,321 and 5,645,851), for the Type II collagen product to be effective it must be prepared in a manner that is retains its natural state. Moore's suggested delivery of this material to the consumer, however, involves the retention of significant amounts of water, thus making the product susceptible to pathogen cross-contamination as well as hydrolysis. Once hydrolyzed and soluble Type II collagen loses its potency in reducing the symptoms of arthritis.

GENERAL DESCRIPTION OF THE INVENTION

The product of the present invention comprises a Type II collagen (collagen II) containing nutraceutical that retains the collagen II in its original crosslinked, insoluble structure in a dehydrated, stabilized form. More specifically the product of the present invention comprises a dehydrated, stabilized articular cartilage, which contains the original crosslinked collagen II in at least 25 wt % concentration which is achieved if at least 80% of the of the original crosslinked collagen II is retained in the dehydrated product. Preferably the dehydration is carried out in a way such as to result in a finely divided form suitable for encapsulation or tabulation. The products of the present invention are obtained by a process which comprises the dehydration and thus stabilization of the articular cartilage at less than traditional processing temperatures in the presence of an ionizable salt that is not harmful to the consumer in the concentrations employed. In a preferred embodiment the articular cartilage is treated with an antimicrobial agent before commination and dehydration. It is believed that the salt stabilizes the collagen II protein in the articular cartilage against hydrolysis and degeneration of the crosslinked structure. During and after processing, the salt also acts as a further antimicrobial stabilizer against growth of pathogens and spoilage organisms during the process, which is oftentimes set at incubation temperatures for the organism of concern, and potential cross contamination.

The main feature of the product of the present invention is that it retains the original structure of the collagen, which it is believed is to a great extent responsible for its beneficial effects in reducing the symptoms of rheumatoid arthritis as well as osteoarthritis.

Another major feature of this invention is that the resulting product maintains its microbial safety for greater than 3 years at room temperature storage conditions. In addition, any deleterious enzyme activity is controlled, resulting in a more desirable commercially attractive product since enzymatic activity can bring about negative organoleptic properties, such as inappropriate odors. In addition, enzymatic activity can negatively affect the efficacy of a natural product.

The procedure employed to produce the product of the present invention provides an improved economic method of converting naturally occurring substances to stable, consumable nutraceuticals that can also be used with other products, which heretofore have been treated with such things as chemical preservatives, thermal processing, irradiation, inert atmospheres, freeze drying, and other antimicrobial stabilization methods.

In the past, a consumable product would not be processed at the temperatures used in the present invention since the resulting products would be organoleptically unacceptable. The recent introduction of the dietary supplement business, where small amounts of material are allowed to be consumed, gives meaning to this invention. Not only are the products of the present invention stable and consumable after long storage periods, but in addition naturally occurring substances retain their natural original structure and thus complete efficacy contained in such substances. As a result improved products are obtained that are useful as dietary supplement, as pharmaceuticals, as over-the-counter medicines, as topical products in creams or lotions (such as a biologically active cream) in medical devices, such as biologically active bandages and as special ingredients in functional foods.

DETAILED DESCRIPTION OF THE INVENTION

The products of the present invention comprise dehydrated products containing a high percentage of collagen II that are obtained under conditions, which maintain the integrity and structure of the collagen II, but still eliminate the majority of pathogens, which could have contaminated the product prior to dehydration The collagen II containing substances are in particular articular cartilage, which is known to contain the highest amount of collagen II of any other cartilage type, bone or other mammalian cells. In general the collagen II content of articular cartilage will vary from 30 to 50% of the dry weight of the cartilage, depending on the type of cartilage and also the method of analysis used to measure the collagen content. In chicken cartilage the collagen II content is 40% or higher by dry weight of the cartilage. Prior to dehydration the water content of articular cartilage can vary from 60 to 85% by weight of the total composition. The crosslinked structure is believed to be the result of not only mechanical entanglement of the collagen II molecules but also covalent and electrostatic binding. In addition, other health beneficial materials such as glucosamines and chondroitin sulfate are part of the overall crosslinked structure of the collagen II in articular cartilage and are retained in the dehydrated products of the present invention. Preferred articular cartilage employed to form the products of the present invention are bovine, shark and chicken cartilage. The most preferred cartilage is chicken sternal cartilage since it contains the highest concentration of collagen II of any articular cartilage.

The process employed to make the products of the present invention involves heating of the articular cartilage at temperatures below which denaturization occurs, and if desirable at reduced pressures, in the presence of an ionizable salt and preferably an antimicrobial agent. In general such temperatures should not exceed 110° F. The salt serves to protect the solid components of the articular cartilage and acts as a stabilizing agent during and after processing to prevent deterioration of the dried product and also protects the collagen II from pathogen and spoilage organism growth during processing temperatures. However it is still preferable to treat the cartilage prior to dehydration with an antimicrobial agent, such as a hypochlorite, a nitrate or nitrite.

The stabilizing salt is an ionizable salt that is safe for consumption and in particular is either sodium or potassium chloride. Salt concentrations vary depending on the cartilage and dehydrating conditions employed. Generally the concentration will range from 5 to 50% by weight of the composition to be dehydrated. Optimum or desirable concentrations can be established experimentally by aging the cartilage and observing the occurrence of an undesirable microbial load. Excess amounts of salt do not prevent the dehydration but may affect the utility of the dehydrated material. In conjunction with the dehydration of collagen II containing chicken cartilage it is preferable to employ a concentration of about 5 to 18% based on the weight of the starting material, which results in a salt concentration of at least 40% as based on the collagen II present in the dehydrated product depending on the accuracy of the test method. The salt is preferably mixed with the particulate cartilage in dry form and then further ground to a uniform mixture before dehydration.

In general the dehydration is conducted until the water content of the starting material is reduced to below 10% by weight and preferably into the range of 1 to 8%. No additional benefit results if the water concentration is reduced even further. At concentrations above 10% stabilization and elimination of microbes may only be partial and inadequate to stabilize the material and the collagen II may still be subject to hydrolysis. In order to permit better mixing of the committed cartilage and the salt it may be desirable to partially reduce the water content before mixing with the salt and complete dehydration. Various additives can be employed to promote a more uniform drying and maintain a free flowing material during the drying. A preferred drying agent is hydroxypropyl methyl cellulose and a preferred flow agent is lecithin.

The use of antimicrobial agents is well known in the art and widely disclosed in the literature. Preferred antimicrobial agents include nitrites and chlorides. An antimicrobial agent, such as sodium hypochlorite, alone or in combination with a suitable acid, such as hydrochloric acid, in solution is added to the starting material to further assist in reducing the initial microbial load. This is particularly the case where the material is also to be stabilized against microbes such as can cause spoilage. The useful concentration range of the antimicrobial agent in parts per million (ppm) is from 10 ppm to 10,000 ppm. Use range of the acid as measured by pH is from pH 4 to pH 10. Strong acid concentrations should be used with care to prevent the release of chlorine gas. When using an antimicrobial agent it is only necessary to soak the material in the agent before subjecting the material to the mixing and drying process.

The material to be dehydrated is generally comminuted so as to allow for even water removal and prevent wet spots in the interior of the particle. The ability to dehydrate evenly increases as the particle size is reduced. The particles, however, should not be reduced to a size where such will affect the structure of the material being dehydrated or cause excessive agglomeration. Particles are preferably reduced to an average size of 0.2 to 0.5" in diameter. After dehydration the dry product can be further comminuted to give a powder suitable for encapsulation or forming into tablets, A wide variety of commercially available drying equipment can be employed in the process of the present invention Preferred equipment is such as permits uniform drying of the material without physically abrading the particles. Fluid bed or rotary drum dryers, which monitor temperature and moisture continuously, are particularly preferred. Release agents and other materials, which aid in the drying of the natural substances, may be added to the drying step. Thus aids that help reduce agglomeration and coating of the walls of the dryer, such as lecithin and hydroxypropyl methylcellulose, are useful in the method of the present invention.

The invention is further illustrated by the following examples.

Example 1

Chicken sternal cartilage is harvested from healthy young (less than 60 days of age) chickens, obtained from a chicken processor. The cartilage was analyzed to contain about 80% water and 20% solids of which 40% was collagen II. The cartilage was washed and soaked three times with 3 parts of an antimicrobial solution of sodium hypochlorite containing about 200 ppm of chlorine for 2 hours. The resulting cartilage then was roughly ground to an average particle size of 0.25" and dried in a fluid bed dryer to reduce the water content by about 50%. The grinding was conducted at temperatures of about 40° F. to prevent any hydrolysis or degeneration of the collagen II during the grinding operation. The comminuted chicken cartilage was then mixed with 8-9% of particulate, dry potassium chloride based on the original weight of the cartilage and again passed through a grinder and reduced to a particles size of about $1/16$" again at a temperature below 40° F. The comminuted chicken cartilage was then dried in a commercially available fluid dryer at temperatures around 102° F. under carefully controlled conditions to make sure that the temperature of the product did not exceed 110° F. at any time until the water content was reduced to below 2%. The resulting product contained approximately 29% by weight of potassium chloride, and 69% of the dried cartilage. Analysis of the dried cartilage using electron microscope (EM) for qualification, and enzyme linked immunosorbent analysis (ELISA) for qualification and quantification, showed the product to contain 28% of undenatured crosslinked collagen II. The presence of the salt also increased the water removal rate as compared to drying the material in the absence of the salt. The dry dehydrated product was then ground into a free flowing powder suitable for pressing into tablets or packing into capsules.

Example 2

It is well known that when chicken cartilage containing collagen II is subjected to conditions such as high temperature for stabilization purposes, that the collagen II molecule denatures and is rendered ineffective regarding the biological activity for the intended purpose.

This example demonstrates the ability of this invention to maintain the undenatured native and biologically active Type II collagen contained in the chicken sternal cartilage, along with microbial product safety and organoleptic properties over time. Product was prepared as in Example 1 using a mixture of 60% chicken sternal cartilage and 40% KCl. The resulting product was studied using four measures; (1) electron microscope (EM) qualification, (2) enzyme linked immunosorbent analysis (ELISA) for qualification and quantification, (3) sequential solubilization/precipitation collagenase specific enzyme analysis (S/PCSE) and, (4) proximate analysis.

EM testing validated that the product of the process of this invention maintains the intact, native, undenatured form regarding the Type II collagen fibrils within the natural chicken sternal cartilage. ELISA testing validated and verified that the product of the process of this invention works to maintain the biologically active Type II collagen for use as intended and can be used for quantification S/PCSE further validated and verified that the process of this invention works to maintain the biologically active Type II collagen for use as intended and can be used for quantification Proximate analysis of the finished product made by this invention confirmed all testing with regards to expected protein percent as compared to reported literature values.

Product produced by this invention was tested at zero time and compared to product stored at room temperature for more than one year. The tests demonstrate that the product is stable for more than a year.

| TIME | Proximate Analysis - Protein* | S/PCSE | ELISA | EM |
|---|---|---|---|---|
| Zero | 12.4% | 11.7% | NA | DETECTED |
| >1 Year | 11.5% | 10.4% | 12.3% | NA |

Note:
NA—Not Available

For comparison purposes, fresh chicken sternal cartilage was subjected to a thermal process that could potentially be used to maintain the product's safety during processing (but not post-processing, due to potential cross contamination). Using S/PCSE analysis it was determined that although the fresh sternum contained about 8% active crosslinked collagen II, after thermally processing at 250° F. for 1 hour, S/PCSE results indicated that less than 1% (almost unmeasureable), if any, of crosslinked collagen II remained in the product.

Example 3

To a mixture of comminuted chicken cartilage and 15% KCl, prepared as described in Example 1, was added 5 parts of hydroxypropyl methylcellulose as a drying agent and 2 parts of lecithin as a flow agent. The mixture when dried in a rotating drum drier, dried more evenly in a shorter time without sticking to the drum as compared to a mixture not containing these additives.

Example 4

100 parts of chicken sternal cartilage is soaked in 300 parts of a solution containing 200 ppm of chlorine at 40° F. for two hours. This soaking step is repeated twice for a minimum of six hours total and the water is filtered off. The cartilage is blended with 15 parts of dry potassium chloride and then repeatedly run through a grinder until a uniform mixture is obtained and the average particle size diameter of the cartilage is reduced to about 1/16". The mixture is then placed in a rotary drum dryer and heated at 104° F. until the water content is reduced to less than 5%. The resulting stabilized material is further ground to a mesh size of 70-100 (0.2 mm to 0.15 mm diameter) and results in a free flowing particulate containing about 60% of dried cartilage of which about 40% was crosslinked collagen II and 38% potassium chloride.

The invention claimed is:

1. A nutraceutical obtained by dehydration of Type II collagen containing cartilage, comprising a mixture of dehydrated particulate cartilage retaining at least 80% of the Type II collagen in its original crosslinked structure, at least 40% by weight of the Type II collagen of an edible ionizable salt and having a water content of less than 10% by weight of the total composition.

2. The product of claim 1, wherein the cartilage is articular cartilage.

3. The product of claim 1, wherein the cartilage is derived from chickens.

4. The product of claim 1 wherein the edible salt is potassium or sodium chloride.

5. The product of claim 1, wherein the cartilage is treated with an antimicrobial agent prior to dehydration.

6. The product of claim 1 wherein the dehydrated product also contains glucosamine and chondroitin.

7. The product of claim 5 wherein the antimicrobial agent is a hypochlorite.

8. The product of claim 1 in the form of a fine powder suitable for forming into tablets and for filling into capsules.

9. The product of claim 1 in the form of a tablet or capsule.

10. The product of claim 1 wherein the cartilage is derived from chicken sternal cartilage.

11. The product of claim 1 wherein the Type II collagen comprises 40 weight % of the dehydrated cartilage.

12. The product of claim 10 wherein the collagen II content of the dehydrated cartilage is 25 weight % or greater.

* * * * *